United States Patent
Lammers

(10) Patent No.: US 6,474,335 B1
(45) Date of Patent: Nov. 5, 2002

(54) ARTIFICIAL RESPIRATION SYSTEM

(75) Inventor: Leonardus Hubertus Maria Lammers, Hoofddorp (NL)

(73) Assignee: Medisize B.V., Hillegom (NL)

( * ) Notice: Subject to any disclaimer, the term of this patent is extended or adjusted under 35 U.S.C. 154(b) by 0 days.

(21) Appl. No.: 09/555,843

(22) PCT Filed: Dec. 1, 1998

(86) PCT No.: PCT/NL98/00681
§ 371 (c)(1),
(2), (4) Date: Jun. 5, 2000

(87) PCT Pub. No.: WO99/27988
PCT Pub. Date: Jun. 10, 1999

(30) Foreign Application Priority Data

Dec. 4, 1997 (NL) ............................................... 1007699

(51) Int. Cl.[7] ................................................. A62B 7/10
(52) U.S. Cl. .............................. 128/205.12; 128/203.16
(58) Field of Search ....................... 128/203.16, 204.15, 128/204.16, 205.12

(56) References Cited

U.S. PATENT DOCUMENTS

| | | | | |
|---|---|---|---|---|
| 3,592,191 A | * | 7/1971 | Jackson ................. | 128/204.16 |
| 3,785,377 A | * | 1/1974 | Jorgensen ............... | 128/205.12 |
| 3,923,057 A | * | 12/1975 | Chalon ................... | 128/203.16 |
| 4,108,172 A | | 8/1978 | Moore, Jr. | |
| 4,232,667 A | | 11/1980 | Chalon et al. ......... | 128/203.26 |
| 4,265,235 A | * | 5/1981 | Fukunaga ............... | 128/205.12 |
| 4,360,018 A | * | 11/1982 | Choksi ................... | 128/205.12 |
| 4,391,271 A | * | 7/1983 | Blanco ................... | 128/205.12 |
| 4,883,051 A | * | 11/1989 | Westenskow et al. .. | 128/205.12 |
| 5,044,361 A | * | 9/1991 | Werner et al. ......... | 128/204.16 |
| 5,231,980 A | * | 8/1993 | Filipovic et al. ....... | 128/205.12 |
| 5,284,160 A | * | 2/1994 | Dryden ................... | 128/205.12 |
| 5,435,298 A | * | 7/1995 | Anthony ................. | 128/203.16 |
| 5,460,172 A | * | 10/1995 | Eckerbom et al. ..... | 128/203.16 |
| 5,471,979 A | * | 12/1995 | Psaros et al. .......... | 128/205.12 |
| 5,487,380 A | * | 1/1996 | Grabenkort ............ | 128/204.15 |
| 5,906,201 A | * | 5/1999 | Nilson ................... | 128/203.16 |

FOREIGN PATENT DOCUMENTS

| | | |
|---|---|---|
| EP | 0 413 127 | 2/1991 |
| EP | 0 533 644 | 3/1993 |
| GB | 2 267 661 | 12/1993 |

* cited by examiner

Primary Examiner—Aaron J. Lewis
(74) Attorney, Agent, or Firm—Young & Thompson

(57) ABSTRACT

A closed circuit is provided in which tube connected to the patient's mouth is connected directly or via a connection tube to a heat-moisture exchanger which, in turn, is connected to the feed and the discharge, respectively, of the respirator. A moisture-removing device is arranged in the feed or discharge.

23 Claims, 2 Drawing Sheets

ARTIFICIAL RESPIRATION SYSTEM

FIELD OF THE INVENTION

The present invention relates to an artificial respiration system for artificial respiration of a patient while metering an anesthetic, with recirculation of the artificial respiration gases and the anesthetic.

BACKGROUND OF THE INVENTION

An artificial respiration system of this type is disclosed in U.S. Pat. No. 4,232,667.

In view of the harmful effects, both on the environment outside an operating theatre and on the staff present in such an operating theatre, when an artificial respiration system is used in combination with anaesthesia by a gas and laughing gas, the aim is increasingly for closed circulation of the respiration gases. That is to say, $CO_2$ is (partially) removed in a controlled manner in the respirator from the gases exhaled by the patient and the gases returned to the patient with the admixture of oxygen and/or anesthetic and/or laughing gas.

The system described in U.S. Pat. No. 5,482,031 has two circuits. A first open circuit is arranged between the heat-moisture exchanger (HME) and the respirator and there is a second circuit between the heat-moisture exchanger and the tube which is inserted into the patient. An air humidifier is present in the latter circuit, so that very moist air circulates in at least the second circuit. It is essential that such a patient inhales air with high moisture. After all, humidification no longer takes place in the nasal and oral cavities because of the short-circuiting with the tube by means of which the air is introduced. Outgoing air is at a relatively high temperature and is therefore able to have a high moisture content. This air cools on moving to the HME. After all, the temperature in an operating theatre is approximately 20° C. Downstream of the HME, the air cools even further. This moisture, which condenses on the walls of the tubing, can easily collect into droplets and a number of droplets can form a water lock, as a result of which the functioning of the equipment is restricted or completely terminated. It is clear that this could constitute a life-threatening situation. Moreover, the $CO_2$ determination is disturbed as a result, so that there is no longer accurate control of the functioning of the patient. Therefore, a variety of constructions have been proposed in the prior art for preventing such a formation of a water lock, but the effect of all these constructions is that the positioning of the various lines remains critical.

A system with recirculation of gases is described in U.S. Pat. No. 4,232,667, cited above. The abovementioned disadvantages are partially eliminated by this means, that is to say large quantities of anesthetic are no longer released into the operating theatre and the use of anesthetic can be restricted, as a result of which the costs decrease. A reduction by a factor of 5–20 with such a system in the case of operations lasting a long time is mentioned as an example. With the system according to U.S. Pat. No. 4,232,667, condensation will doubtless be produced, as a result of which liquid will be formed in the lines connected to the patient. The figures that the lines from the respirator all run downwards, so that such moisture moves back towards the patient.

This system does not operate satisfactorily. After all, in practice tubing will always be set up so that it is movable to some degree with respect to the patient, that is to say the lowest point of the tubing will not be the patient, but will be located at a point between the respirator and the mouth of the patient. Consequently, if there is condensation a water lock can be produced, with all the associated consequences.

Furthermore, it is a fact that although it will in general be possible for the lungs to cope with water supplied to the patient, if there is ingress of water into the lungs a reaction occurs which is not beneficial for the stability of the patient during the operation. The system according to said U.S. Patent is comparable with an active humidifying system.

British Patent 2 267 661 discloses a heat-moisture exchanger (HME), as well as a method for testing the latter. Comparison tests are proposed with a construction that simulates the patient and respirator in which, in one case, an HME is incorporated and, in the other case, such a heat-moisture exchanger is not present. This testing bears great similarity to the method specified in ISO 9360. In order to preclude the influence of moisture in the respirator. a separate driving device is present. In no way is it the intention to use the test set-ups proposed in the British Patent on patients. The system described in the British Patent is comparable with a passive humidifying system, the artificial respiration tubes remaining completely dry.

SUMMARY OF THE INVENTION

The aim of the present invention is to provide an artificial respiration system wherein, without risk to the patient, the various lines can be positioned in a simple manner without taking account of the possibility of blockages as a result of a water lock.

This aim is realised with an artificial respiration system as described the hereafter.

The invention is based on the insight of, in contrast to the prior art, in which the air is always kept as moist as possible and blockage of the lines in critical locations has to be prevented by special measures, keeping the air in the first circuit as dry as possible and dispensing with the second circuit as far as possible. This is possible by positioning the heat-moisture exchanger close to the mouth of the patient and fitting the tube to be inserted in the patient's pharynx directly (if necessary via a connector) to the heat-moisture exchanger. As a result of this there is no risk of blockage caused by a water lock in the second part. Moisture-removing means are placed in the first circuit, by means of which any moisture that passes through the heat-moisture exchanger if this is not operating 100% is captured and removed.

The system described above is used in a particularly advantageous manner in a closed system, that is to say a system in which air exhaled by the patient is fed back via the HME to the equipment, $CO_2$ being removed in the system and fresh oxygen with anesthetic and, if appropriate, laughing gas being supplied. A further variant of a closed system of this type is that in which a large quantity of air with anesthetic and further necessary additives is circulated and air is tapped off at a specific point in the system and metered via an HME to the patient. Air exhaled by the patient is fed back to the system. A system of this type is known under the name 'PhysioFlex'.

Furthermore, it is possible with this construction with recycling of the exhaled air to determine the percentage of $CO_2$ in said exhaled air close to the heat-moisture exchanger accurately. and with a reduced risk of disturbances. Such measurements are no longer unstable because of condensed moisture which can be present. Consequently, control of oxygen metering can be effected more accurately. In some cases the air flow is monitored by measuring the pressure drop over a certain section of the lines. Disturbances can arise if moisture is present in the lines, in the measurement tubes or, respectively, the measurement probe. Such disturbances are circumvented by the construction according to the invention.

The moisture-removing means can be installed at any location in the system. Examples are the discharge from the patient, in the $CO_2$ measurement line, in the feed to the patient and combined with the $CO_2$ removal device. Furthermore, it is possible to install moisture-removing means at various locations. If a $CO_2$-removing device is used, the preference is for installation of the drying means downstream of the $CO_2$-removing means in the respirator. By this means the moisture which is produced during the removal of $CO_2$ if, for example, a calcium hydroxide or barium hydride system is used, can also be removed.

The moisture-removing means can be any construction disclosed in the prior art or any conceivable construction, such as means operating by absorption (for example using silica gel) or means operating by condensation. The actual means used are dependent on the application concerned. The moisture-removing means are preferably integrated in the respirator.

With the construction described above it is now possible to arrange the feed and discharge coaxially with respect to one another. After all, it is no longer necessary to check the various tubes and to run these in a specific manner because there is no risk of water locks. By fitting the tubes inside one another it is possible to use simple, standardised coupling means, both to the respirator and to the heat-moisture exchanger. In this way it is possible to leave the respirator behind in the operating theatre after the operation and to connect the patient to a different respirator via the free ends of the tubes which remain connected, with the heat-moisture exchanger, to the patient. These tubes can, for example, be coupled to a respirator located in the intensive care unit.

BRIEF DESCRIPTION OF THE DRAWINGS

The invention will be explained in more detail below with reference to illustrative embodiments shown in the drawing. In the drawing.

DETAILED DESCRIPTION OF THE PREFERRED EMBODIMENTS

Figure 1:
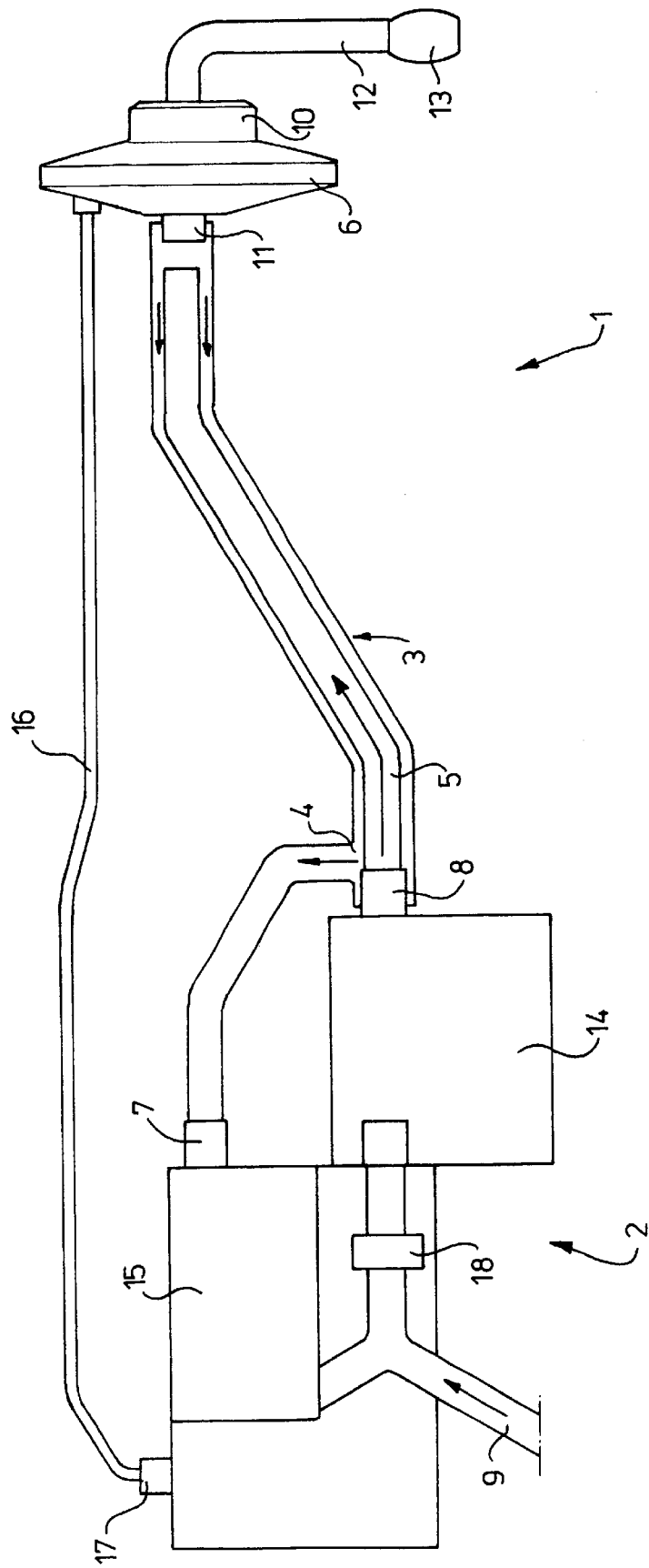
FIG. 1 shows, highly diagrammatically, a first embodiment of the artificial respiration system according to the invention.

In FIG. 1 the artificial respiration system according to the invention is indicated in its entirety by 1. The system consists of a respirator 2, a coaxial tube 3, which is connected to a heat-moisture exchanger 6, and a tube 12, which is connected to the heat-moisture exchanger and is introduced inside the patient via a cuff 13.

Respirator 2 is provided with an inlet 7 for air originating from tube section 4. This air is passed from inlet 7 through chamber 15, where $CO_2$ is removed. The condition of the patient and his/her lung function is determined by an active suction $CO_2$ measurement probe 17 which is fitted at the end of a line 16 which opens into the heat-moisture exchanger. $CO_2$ measurement is stable in this way. Oxygen, anesthetic and laughing gas and further additives as desired are fed in a controlled manner via line 9 to the discharge from chamber 15. This control can be realised in any way known from the prior art. A ventilator 18 then follows and a drying chamber 14, which operates by means of absorption, is connected in series downstream thereof. The drying chamber is filled with silica gel. The outlet 8 thereof opens into line section 5 of coaxial tube 3. Coaxial tube 3 opens into the inlet 11 of the heat-moisture exchanger 6.

Figure 2:
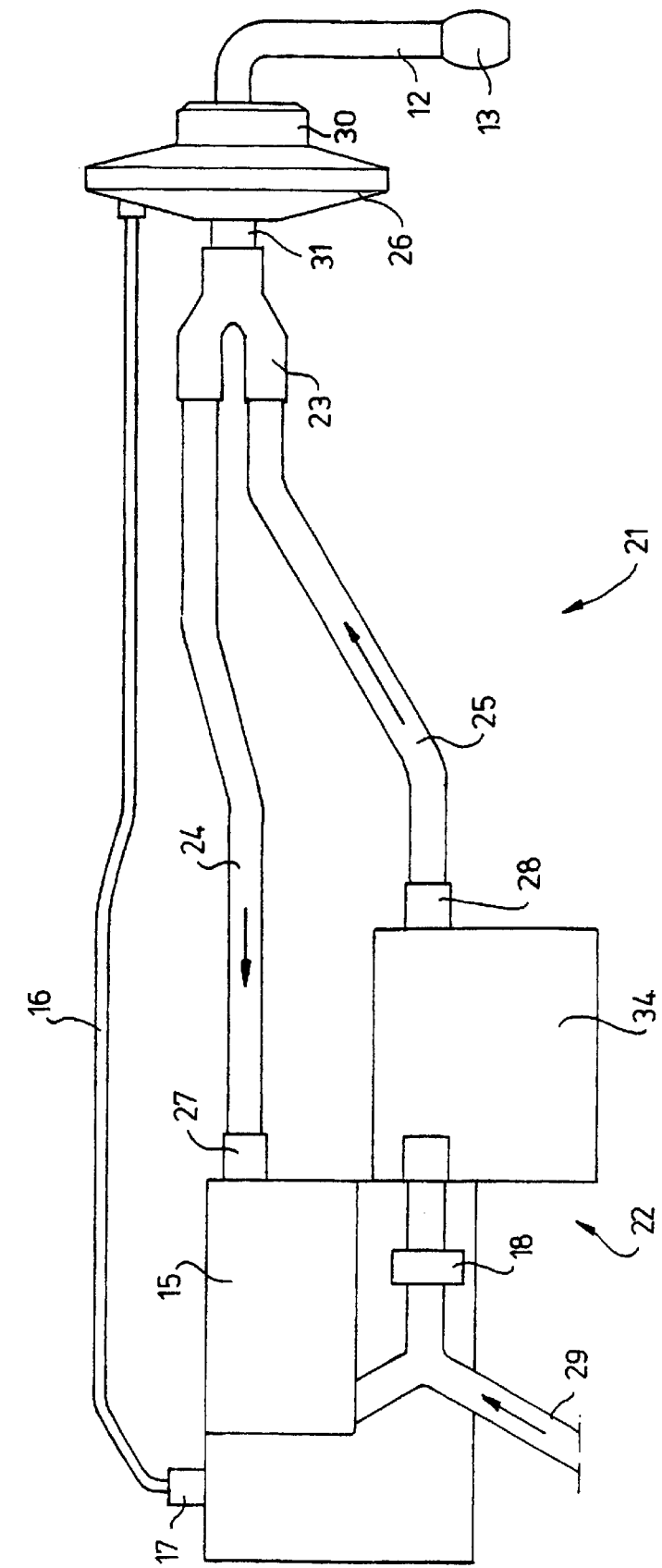
FIG. 2 shows a second embodiment thereof.

FIG. 2 shows a variant of the above construction which is indicated in its entirety by 21. This variant consists of a respirator 22 which is essentially identical to the construction described above. Corresponding components are provided with the same reference numerals. There is now no question of a coaxial tube but of two separate lines, the discharge from the patient being indicated by 24 and the feed to the patient being indicated by 25. The lines open, respectively, into inlet 27 and outlet 28 of system 22. The supply of oxygen and anesthetic is indicated by 29. Tubes 24 and 25 open into Y-piece 23, which is connected to the inlet 31 of the heat-moisture exchanger (or HME). 34 indicates drying equipment operating by means of condensation.

In FIG. 2 other locations of the moisture-removing means 34' are shown in dotted lines.

The heat-moisture exchanger can be any heat-moisture exchanger known from the prior art.

With both types of equipment described above, moisture present downstream of the heat-moisture exchanger, that is to say in line 4 and line 24, respectively, which moisture content can also rise as a result of reaction which takes place in chamber 15, is captured and removed in chamber 14 and chamber 34, respectively. In this context the amount of moisture which must be removed is always such that no moisture condenses even at the lowest temperature (outside the dryer) which occurs in the system.

It has been found that the patient suffers no disadvantage whatsoever from such essentially dry feed and discharge. Moreover, there is no risk of blockage of lines 3 and 24, 25, respectively, by the production of water locks and $CO_2$ measurement is not disturbed.

For determination of the capacity of the equipment for the removal of water 14, 34 it is, of course, necessary to take into account the quantity of moisture which passes through the heat-moisture exchanger and the quantity of moisture which may be liberated in chamber 15. In particular, the quality of the heat-moisture exchanger is important. Under operating conditions the following values can be taken as an example:

Air to be inhaled preferably contains more than 30 mg $H_2O$ per litre air.

Water loss through a heat-moisture exchanger is less than 10 mg $H_2O$ per litre air. Depending on the body weight and other factors, between 2 litres (new born babies) and 10 litres (large adults) air per minute is used for artificial respiration of a patient. During artificial respiration approximately 0.5 litre fresh gas per minute is supplied and approximately 14 ml $H_2O$ per hour is produced in the system.

An adult with a normal metabolism produces 15 mol $CO_2$ per 24 hours ($CO_2$ is converted 1:1 to $H_2O$ in chamber 15).

The operating theatre temperature is usually approximately 20° C.

Based on the above average values, a breath volume per minute of 8/min and an operating time of 1 hour, the total quantity of water which has to be removed by chamber 14 or 34, respectively, is 14 ml per operation. For the above, complete removal of $CO_2$ with so-called 'soda lime' has been assumed. If less $CO_2$ is removed, the quantity of water liberated during this operation will, of course, fall and the system will be adapted accordingly.

Although the invention has been described above with reference to a preferred embodiment, it will be clear that numerous variants of the circuit feed and discharge are possible and that it is possible to position the moisture-removing means at any other location in such a circuit. Such variants are all considered to fall within the scope of the appended claims.

What is claimed is:

1. Artificial respiration system for artificial respiration of a patient while metering an anesthetic, with recirculation of the artificial respiration gases and the anesthetic comprising a respirator having an inlet connected to the discharge from a patient, an outlet connected to a feed to a patient, as well as metering means for metering an anesthetic and/or laughing gas and oxygen into said feed, said feed and discharge merging into a common component which is provided with a tube to be inserted into the patient's pharynx and is provided with $CO_2$-removing equipment, wherein said tube is connected to one side of a heat-moisture exchanger (HME), said feed and discharge are connected to the other side of the heat-moisture exchanger and a moisture remover is in the respirator.

2. Artificial respiration system according to claim 1, wherein said moisture-remover comprises absorption-drying equipment.

3. Artificial respiration system according to claim 1, wherein said moisture-remover comprises condensation-drying means.

4. Artificial respiration system according to claim 1, further comprising adsorption means arranged in the $CO_2$-removing equipment.

5. Artificial respiration system according to claim 1, wherein said feed and discharge are arranged coaxially with respect to one another.

6. Artificial respiration system for artificial respiration of a patient while metering an anesthetic, with recirculation of the artificial respiration gases and the anesthetic comprising a respirator having an inlet connected to the discharge from a patient, an outlet connected to a feed to a patient, as well as metering means for metering an anesthetic and/or laughing gas and oxygen into said feed, said feed and discharge merging into a common component which is provided with a tube to be inserted into the patient's pharynx and is provided with $CO_2$-removing equipment, wherein said tube is connected to one side of a heat-moisture exchanger (HME), said feed and discharge are connected to the other side of the heat-moisture exchanger and a moisture remover is in the respirator, wherein said moisture-remover is installed downstream of said $CO_2$-removing equipment.

7. Artificial respiration system for artificial respiration of a patient while metering an anesthetic, with recirculation of the artificial respiration gases and the anesthetic comprising a respirator having an inlet connected to the discharge from a patient, an outlet connected to a feed to a patient, as well as metering means for metering an anesthetic and/or laughing gas and oxygen into said feed, said feed and discharge merging into a common component which is provided with a tube to be inserted into the patient's pharynx and is provided with $CO_2$-removing equipment, wherein said tube is connected to one side of a heat-moisture exchanger (HME), said feed and discharge are connected to the other side of the heat-moisture exchanger and a moisture remover is in the feed.

8. Artificial respiration system according to claim 7, wherein said moisture remover is installed downstream of said $CO_2$-removing equipment.

9. Artificial respiration system according to claim 7, wherein said moisture-remover comprises absorption-drying equipment.

10. Artificial respiration system according to claim 7, wherein said moisture-remover comprises condensation-drying means.

11. Artificial respiration system according to claim 7, further comprising adsorption means arranged in the $CO_2$-removing equipment.

12. Artificial respiration system according to claim 7, wherein said feed and discharge are arranged coaxially with respect to one another.

13. Artificial respiration system for artificial respiration of a patient while metering an anesthetic, with recirculation of the artificial respiration gases and the anesthetic comprising a respirator having an inlet connected to the discharge from a patient, an outlet connected to a feed to a patient, as well as metering means for metering an anesthetic and/or laughing gas and oxygen into said feed, said feed and discharge merging into a common component which is provided with a tube to be inserted into the patient's pharynx and is provided with $CO_2$-removing equipment, wherein said tube is connected to one side of a heat-moisture exchanger (HME), said feed and discharge are connected to the other side of the heat-moisture exchanger and a moisture remover is in the discharge.

14. Artificial respiration system according to claim 13, wherein said moisture-remover is installed downstream of said $CO_2$-removing equipment.

15. Artificial respiration system according to claim 13, wherein said moisture-remover comprises absorption-drying equipment.

16. Artificial respiration system according to claim 13, wherein said moisture-remover comprises condensation-drying means.

17. Artificial respiration system according to claim 13, further comprising adsorption means arranged in the $CO_2$-removing equipment.

18. Artificial respiration system according to claim 13, wherein said feed and discharge are arranged coaxially with respect to one another.

19. Artificial respiration system for artificial respiration of a patient while metering an anesthetic, with recirculation of the artificial respiration gases and the anesthetic comprising a respirator having an inlet connected to the discharge from a patient, an outlet connected to a feed to a patient, as well as metering means for metering an anesthetic and/or laughing gas and oxygen into said feed, said feed and discharge merging into a common component which is provided with a tube to be inserted into the patient's pharynx and is provided with $CO_2$-removing equipment, wherein said tube is connected to one side of a heat-moisture exchanger (HME), said feed and discharge are connected to the other side of the heat-moisture exchanger and a moisture remover is in the $CO_2$ removing equipment.

20. Artificial respiration system according to claim 19, wherein said moisture-remover comprises absorption-drying equipment.

21. Artificial respiration system according to claim 19, wherein said moisture-remover comprises condensation-drying means.

22. Artificial respiration system according to claim 19, further comprising adsorption means arranged in the $CO_2$-removing equipment.

23. Artificial respiration system according to claim 19, wherein said feed and discharge are arranged coaxially with respect to one another.

* * * * *